United States Patent
Lee et al.

(10) Patent No.: US 9,693,823 B2
(45) Date of Patent: Jul. 4, 2017

(54) SYSTEM AND METHOD FOR TREATING TISSUE USING AN EXPANDABLE ANTENNA

(71) Applicant: COVIDIEN LP, Mansfield, MA (US)

(72) Inventors: Anthony C. Lee, San Francisco, CA (US); Kenlyn S. Bonn, Lakewood, CO (US); Mani N. Prakash, Boulder, CO (US); Francesca Rossetto, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/806,080

(22) Filed: Jul. 22, 2015

(65) Prior Publication Data

US 2015/0320496 A1   Nov. 12, 2015

Related U.S. Application Data

(62) Division of application No. 13/344,790, filed on Jan. 6, 2012, now Pat. No. 9,119,648.

(51) Int. Cl.
*A61B 18/18* (2006.01)
*A61B 18/00* (2006.01)

(52) U.S. Cl.
CPC *A61B 18/1815* (2013.01); *A61B 2018/00214* (2013.01); *A61B 2018/00267* (2013.01); *A61B 2018/00577* (2013.01); *A61B 2018/00601* (2013.01); *A61B 2018/1861* (2013.01); *A61B 2018/1869* (2013.01)

(58) Field of Classification Search
CPC ............ A61B 18/1815; A61B 18/1492; A61B 2018/00214; A61B 18/18; A61B 2018/00577; A61B 18/00; A61B 2018/00267; A61B 2018/00601; A61B 2017/00292; A61B 17/00234; A61N 5/02; A61N 1/08; A61N 1/40; A61N 5/00; A61M 2025/1088; A61M 2025/0004
See application file for complete search history.

(56) References Cited

U.S. PATENT DOCUMENTS

| | | | |
|---|---|---|---|
| 3,631,363 | A | 12/1971 | Miller |
| D223,367 | S | 4/1972 | Kountz |
| D263,020 | S | 2/1982 | Rau, III |
| D266,842 | S | 11/1982 | Villers et al. |
| 4,397,313 | A | 8/1983 | Vaguine |

(Continued)

FOREIGN PATENT DOCUMENTS

| | | |
|---|---|---|
| CN | 1103807 A | 6/1995 |
| CN | 101553181 A | 10/2009 |

(Continued)

OTHER PUBLICATIONS

Medtrex Brochure "The O.R. Pro 300" 1 page, Sep. 1998.

(Continued)

*Primary Examiner* — Deborah Malamud

(57) ABSTRACT

An ablation device includes an antenna assembly having a radiating portion configured to deliver energy from a power source to tissue of a patient. The radiating portion has an outer conductor and an inner conductor extending therethrough. The inner conductor is disposed within the outer conductor and defines a longitudinal axis. One of the inner conductor and the outer conductor is movable relative to the other to cause at least a portion of the outer conductor to expand radially relative to the longitudinal axis.

13 Claims, 4 Drawing Sheets

(56) References Cited

U.S. PATENT DOCUMENTS

| | | |
|---|---|---|
| 4,462,412 A | 7/1984 | Turner |
| D278,306 S | 4/1985 | McIntosh |
| 4,572,190 A | 2/1986 | Azam et al. |
| 4,643,186 A | 2/1987 | Rosen et al. |
| D295,893 S | 5/1988 | Sharkany et al. |
| D295,894 S | 5/1988 | Sharkany et al. |
| 4,798,215 A | 1/1989 | Turner |
| 5,057,106 A | 10/1991 | Kasevich et al. |
| 5,097,844 A | 3/1992 | Turner |
| 5,248,312 A | 9/1993 | Langberg |
| 5,257,635 A | 11/1993 | Langberg |
| 5,275,597 A | 1/1994 | Higgins et al. |
| 5,281,217 A | 1/1994 | Edwards et al. |
| 5,364,392 A | 11/1994 | Warner et al. |
| 5,366,490 A | 11/1994 | Edwards et al. |
| 5,370,675 A | 12/1994 | Edwards et al. |
| D354,218 S | 1/1995 | Van de Peer |
| 5,405,346 A | 4/1995 | Grundy et al. |
| 5,417,210 A | 5/1995 | Funda et al. |
| 5,470,308 A | 11/1995 | Edwards et al. |
| 5,472,441 A | 12/1995 | Edwards et al. |
| 5,507,743 A | 4/1996 | Edwards et al. |
| 5,536,240 A | 7/1996 | Edwards et al. |
| 5,536,267 A | 7/1996 | Edwards et al. |
| 5,556,377 A | 9/1996 | Rosen et al. |
| 5,558,673 A | 9/1996 | Edwards et al. |
| 5,562,720 A | 10/1996 | Stern et al. |
| 5,571,147 A | 11/1996 | Sluijter et al. |
| 5,599,294 A | 2/1997 | Edwards et al. |
| 5,599,295 A | 2/1997 | Rosen et al. |
| 5,607,389 A | 3/1997 | Edwards et al. |
| 5,693,082 A | 12/1997 | Warner et al. |
| 5,720,718 A | 2/1998 | Rosen et al. |
| 5,722,401 A | 3/1998 | Pietroski et al. |
| 5,776,176 A | 7/1998 | Rudie |
| 5,800,484 A | 9/1998 | Gough et al. |
| 5,800,486 A | 9/1998 | Thome et al. |
| 5,800,494 A | 9/1998 | Campbell et al. |
| 5,846,238 A | 12/1998 | Jackson et al. |
| 5,861,021 A | 1/1999 | Thome et al. |
| 5,863,290 A | 1/1999 | Gough et al. |
| 5,871,525 A | 2/1999 | Edwards et al. |
| 5,902,251 A | 5/1999 | vanHooydonk |
| 5,921,982 A | 7/1999 | Lesh et al. |
| 5,951,547 A | 9/1999 | Gough et al. |
| 5,957,969 A | 9/1999 | Warner et al. |
| 5,964,755 A | 10/1999 | Edwards |
| 6,016,452 A | 1/2000 | Kasevich |
| 6,024,740 A | 2/2000 | Lesh et al. |
| 6,031,375 A | 2/2000 | Atalar et al. |
| 6,047,216 A | 4/2000 | Carl et al. |
| 6,052,607 A | 4/2000 | Edwards et al. |
| D424,693 S | 5/2000 | Pruter |
| D424,694 S | 5/2000 | Tetzlaff et al. |
| D425,201 S | 5/2000 | Tetzlaff et al. |
| 6,056,744 A | 5/2000 | Edwards |
| 6,117,101 A | 9/2000 | Diederich et al. |
| 6,210,367 B1 | 4/2001 | Carr |
| 6,223,086 B1 | 4/2001 | Carl et al. |
| 6,226,553 B1 | 5/2001 | Carl et al. |
| 6,245,064 B1 | 6/2001 | Lesh et al. |
| 6,246,912 B1 | 6/2001 | Sluijter et al. |
| 6,290,715 B1 | 9/2001 | Sharkey et al. |
| D449,886 S | 10/2001 | Tetzlaff et al. |
| 6,306,132 B1 | 10/2001 | Moorman et al. |
| 6,350,276 B1 | 2/2002 | Knowlton |
| 6,355,033 B1 | 3/2002 | Moorman et al. |
| 6,375,606 B1 | 4/2002 | Garibaldi et al. |
| D457,958 S | 5/2002 | Dycus et al. |
| D457,959 S | 5/2002 | Tetzlaff et al. |
| 6,413,255 B1 | 7/2002 | Stern |
| 6,419,653 B2 | 7/2002 | Edwards et al. |
| 6,425,912 B1 | 7/2002 | Knowlton |
| 6,430,446 B1 | 8/2002 | Knowlton |
| 6,451,015 B1 | 9/2002 | Rittman, III et al. |
| 6,477,426 B1 | 11/2002 | Fenn et al. |
| 6,496,736 B1 | 12/2002 | Carl et al. |
| 6,496,738 B2 | 12/2002 | Carr |
| 6,514,249 B1 | 2/2003 | Maguire et al. |
| 6,526,320 B2 | 2/2003 | Mitchell |
| 6,547,788 B1 | 4/2003 | Maguire et al. |
| 6,551,311 B2 | 4/2003 | Lee et al. |
| 6,569,159 B1 | 5/2003 | Edwards et al. |
| 6,582,426 B2 | 6/2003 | Moorman et al. |
| 6,599,288 B2 | 7/2003 | Maguire et al. |
| 6,603,994 B2 | 8/2003 | Wallace et al. |
| 6,610,054 B1 | 8/2003 | Edwards et al. |
| 6,622,731 B2 | 9/2003 | Daniel et al. |
| 6,652,515 B1 | 11/2003 | Maguire et al. |
| 6,652,520 B2 | 11/2003 | Moorman et al. |
| 6,673,070 B2 | 1/2004 | Edwards et al. |
| D487,039 S | 2/2004 | Webster et al. |
| 6,725,080 B2 | 4/2004 | Melkent et al. |
| 6,788,977 B2 | 9/2004 | Fenn et al. |
| D496,997 S | 10/2004 | Dycus et al. |
| D499,181 S | 11/2004 | Dycus et al. |
| 6,847,848 B2 | 1/2005 | Sterzer et al. |
| 6,852,091 B2 | 2/2005 | Edwards et al. |
| 6,869,431 B2 | 3/2005 | Maguire et al. |
| 6,878,147 B2 | 4/2005 | Prakash et al. |
| 6,932,776 B2 | 8/2005 | Carr |
| 6,997,925 B2 | 2/2006 | Maguire et al. |
| D525,361 S | 7/2006 | Hushka |
| 7,089,063 B2 | 8/2006 | Lesh et al. |
| D531,311 S | 10/2006 | Guerra et al. |
| 7,118,590 B1 | 10/2006 | Cronin |
| 7,128,739 B2 | 10/2006 | Prakash et al. |
| D533,942 S | 12/2006 | Kerr et al. |
| 7,147,632 B2 | 12/2006 | Prakash et al. |
| D535,027 S | 1/2007 | James et al. |
| 7,160,292 B2 | 1/2007 | Moorman et al. |
| 7,160,296 B2 | 1/2007 | Pearson et al. |
| 7,160,299 B2 | 1/2007 | Baily |
| 7,186,251 B2 | 3/2007 | Malecki et al. |
| D541,418 S | 4/2007 | Schechter et al. |
| D541,938 S | 5/2007 | Kerr et al |
| 7,252,665 B2 | 8/2007 | Starkebaum et al. |
| 7,267,683 B2 | 9/2007 | Sharkey et al. |
| 7,276,061 B2 | 10/2007 | Schaer et al. |
| 7,278,991 B2 | 10/2007 | Morris et al. |
| 7,282,050 B2 | 10/2007 | Starkebaum et al. |
| 7,282,061 B2 | 10/2007 | Sharkey et al. |
| 7,291,146 B2 | 11/2007 | Steinke et al. |
| 7,311,703 B2 | 12/2007 | Turovskiy et al. |
| 7,318,824 B2 | 1/2008 | Prakash et al. |
| 7,326,201 B2 | 2/2008 | Fjield et al. |
| D564,662 S | 3/2008 | Moses et al. |
| 7,344,533 B2 | 3/2008 | Pearson et al. |
| 7,371,235 B2 | 5/2008 | Thompson et al. |
| 7,387,626 B2 | 6/2008 | Edwards et al. |
| 7,399,299 B2 | 7/2008 | Daniel et al. |
| D576,932 S | 9/2008 | Strehler |
| 7,422,586 B2 | 9/2008 | Morris et al. |
| 7,439,736 B2 | 10/2008 | Meaney et al. |
| 7,465,300 B2 | 12/2008 | Arless et al. |
| 7,467,015 B2 | 12/2008 | van der Weide |
| D594,736 S | 6/2009 | Esjunin |
| D594,737 S | 6/2009 | Kelly et al. |
| 7,565,207 B2 | 7/2009 | Turner et al. |
| 7,615,049 B2 | 11/2009 | West et al. |
| D606,203 S | 12/2009 | Husheer et al. |
| 7,642,451 B2 | 1/2010 | Bonn |
| D613,412 S | 4/2010 | DeCarlo |
| 7,875,024 B2 | 1/2011 | Turovskiy et al. |
| D634,010 S | 3/2011 | DeCarlo |
| 8,035,570 B2 | 10/2011 | Prakash et al. |
| 8,059,059 B2 | 11/2011 | Bonn |
| 8,118,808 B2 | 2/2012 | Smith et al. |
| 8,182,480 B2 | 5/2012 | Huseman |
| 8,192,427 B2 | 6/2012 | Buysse |
| 8,197,473 B2 | 6/2012 | Rossetto et al. |
| 8,202,270 B2 | 6/2012 | Rossetto et al. |
| 8,211,098 B2 | 7/2012 | Paulus |
| 8,211,099 B2 | 7/2012 | Buysse et al. |

(56) References Cited

U.S. PATENT DOCUMENTS

| | | |
|---|---|---|
| 8,216,227 B2 | 7/2012 | Podhajsky |
| 8,221,418 B2 | 7/2012 | Prakash et al. |
| 8,235,981 B2 | 8/2012 | Prakash et al. |
| 8,246,614 B2 | 8/2012 | DeCarlo |
| 8,251,987 B2 | 8/2012 | Willyard |
| 8,262,703 B2 | 9/2012 | Prakash et al. |
| 8,292,880 B2 | 10/2012 | Prakash et al. |
| 8,292,881 B2 | 10/2012 | Brannan et al. |
| 8,343,149 B2 | 1/2013 | Rossetto et al. |
| 8,353,902 B2 | 1/2013 | Prakash |
| 8,353,903 B2 | 1/2013 | Podhajsky |
| 8,394,086 B2 | 3/2013 | Behnke et al. |
| 8,435,237 B2 | 5/2013 | Bahney |
| 8,463,396 B2 | 6/2013 | Podhajsky |
| 8,512,328 B2 | 8/2013 | Rossetto et al. |
| 8,834,409 B2 | 9/2014 | Manley |
| 8,834,460 B2 | 9/2014 | Peterson |
| 8,945,111 B2 | 2/2015 | Brannan et al. |
| 8,965,536 B2 | 2/2015 | Bonn et al. |
| 9,113,924 B2 | 8/2015 | Brannan et al. |
| 9,119,648 B2 | 9/2015 | Lee et al. |
| 9,173,706 B2 | 11/2015 | Rossetto |
| 9,198,723 B2 | 12/2015 | Paulus et al. |
| 2002/0022836 A1 | 2/2002 | Goble et al. |
| 2002/0120261 A1 | 8/2002 | Morris et al. |
| 2003/0032951 A1 | 2/2003 | Rittman et al. |
| 2003/0195499 A1 | 10/2003 | Prakash et al. |
| 2004/0097805 A1 | 5/2004 | Verard et al. |
| 2004/0242992 A1 | 12/2004 | Hareyama |
| 2005/0038419 A9 | 2/2005 | Arnold et al. |
| 2005/0096647 A1 | 5/2005 | Steinke et al. |
| 2005/0137662 A1 | 6/2005 | Morris et al. |
| 2005/0149010 A1 | 7/2005 | Turovskiy et al. |
| 2005/0197570 A1 | 9/2005 | Carr |
| 2005/0203388 A1 | 9/2005 | Carr |
| 2005/0228370 A1 | 10/2005 | Sterzer et al. |
| 2005/0240239 A1 | 10/2005 | Boveja et al. |
| 2005/0256521 A1 | 11/2005 | Kozel |
| 2006/0015162 A1 | 1/2006 | Edward et al. |
| 2006/0030914 A1 | 2/2006 | Eggers et al. |
| 2006/0106375 A1 | 5/2006 | Werneth et al. |
| 2006/0264923 A1 | 11/2006 | Prakash et al. |
| 2006/0282069 A1 | 12/2006 | Prakash et al. |
| 2006/0293650 A1 | 12/2006 | Prakash et al. |
| 2006/0293651 A1 | 12/2006 | Cronin |
| 2007/0060989 A1 | 3/2007 | Deem et al. |
| 2007/0156140 A1 | 7/2007 | Baily |
| 2007/0161977 A1 | 7/2007 | Moorman et al. |
| 2007/0191825 A1 | 8/2007 | Cronin et al. |
| 2007/0219546 A1 | 9/2007 | Mody et al. |
| 2007/0233057 A1 | 10/2007 | Konishi |
| 2007/0299434 A1 | 12/2007 | Malecki et al. |
| 2008/0308256 A1 | 12/2008 | Deborski et al. |
| 2009/0192508 A1 | 7/2009 | Laufer et al. |
| 2009/0248005 A1 | 10/2009 | Rusin et al. |
| 2009/0306652 A1 | 12/2009 | Buysse et al. |
| 2010/0030206 A1 | 2/2010 | Brannan et al. |
| 2010/0030210 A1 | 2/2010 | Paulus |
| 2010/0045559 A1 | 2/2010 | Rossetto |
| 2010/0049189 A1 | 2/2010 | Dickens |
| 2010/0076422 A1 | 3/2010 | Podhajsky |
| 2010/0087808 A1 | 4/2010 | Paulus |
| 2010/0094273 A1 | 4/2010 | Rossetto et al. |
| 2010/0256624 A1 | 10/2010 | Brannan et al. |
| 2010/0262134 A1 | 10/2010 | Jensen et al. |
| 2012/0004650 A1 | 1/2012 | Shiu et al. |
| 2014/0214017 A1 | 7/2014 | Brannan |
| 2014/0214023 A1 | 7/2014 | Prakash et al. |
| 2014/0257267 A1 | 9/2014 | Shiu et al. |
| 2014/0290045 A1 | 10/2014 | Bonn |
| 2014/0296840 A1 | 10/2014 | Behnke |
| 2014/0296841 A1 | 10/2014 | Brannan |
| 2015/0065944 A1 | 3/2015 | Ohri et al. |
| 2015/0065964 A1 | 3/2015 | Ohri et al. |
| 2015/0305809 A1 | 10/2015 | Prakash et al. |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 481 685 A1 | 4/1992 |
| EP | 0 521 264 A2 | 1/1993 |
| EP | 0541930 A1 | 5/1993 |
| EP | 0 556 705 A1 | 8/1993 |
| EP | 0 558 429 A1 | 9/1993 |
| EP | 0572131 A1 | 12/1993 |
| EP | 0 648 515 A1 | 4/1995 |
| EP | 0 667 126 A1 | 8/1995 |
| EP | 0 836 868 A2 | 4/1998 |
| EP | 0 882 955 A1 | 12/1998 |
| EP | 0908156 A1 | 4/1999 |
| EP | 1 070 518 A2 | 1/2001 |
| EP | 1186274 A2 | 3/2002 |
| EP | 1278007 A1 | 1/2003 |
| EP | 1159926 A3 | 3/2003 |
| EP | 1 810 827 A1 | 7/2007 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| GB | 2388039 A | 11/2003 |
| JP | 5-5106 | 1/1993 |
| JP | 05-40112 | 2/1993 |
| JP | 06343644 A | 12/1994 |
| JP | 07265328 A | 10/1995 |
| JP | 08056955 | 3/1996 |

(56) References Cited

FOREIGN PATENT DOCUMENTS

| | | |
|---|---|---|
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 94/04220 A1 | 3/1994 |
| WO | 9604860 A1 | 2/1996 |
| WO | 97/41924 A1 | 11/1997 |
| WO | 97/43971 A2 | 11/1997 |
| WO | 97/48450 A1 | 12/1997 |
| WO | 00/13602 A2 | 3/2000 |
| WO | 0012010 A1 | 3/2000 |
| WO | 00/48672 A1 | 8/2000 |
| WO | 00/49957 A1 | 8/2000 |
| WO | 00/51513 A1 | 9/2000 |
| WO | 00/53113 A1 | 9/2000 |
| WO | 01/01847 A1 | 1/2001 |
| WO | 01/74252 A2 | 10/2001 |
| WO | 02/45790 A2 | 6/2002 |
| WO | 02/061880 A2 | 8/2002 |
| WO | 2004112628 A1 | 12/2004 |
| WO | 2005/011049 A2 | 2/2005 |
| WO | 2005/016119 A2 | 2/2005 |
| WO | 2006/105121 A2 | 10/2006 |
| WO | 2010/035831 A1 | 4/2010 |

OTHER PUBLICATIONS

Michael Choti, "Abdominoperineal Resection with the LigaSure.™. Vessel Sealing System and LigaSure.™. Atlas 20 cm Open Instrument" Innovations That Work, Jun. 2003.
Muller et al., "Extended Left Hemicolectomy Using the LigaSure.™. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.™. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.cndot. Vessel Sealing System in Minimally Invasive Surgery in Children" Int'l Pediatric Endosurgery Group (I Peg) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.™. Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.™. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.

(56) References Cited

OTHER PUBLICATIONS

European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
International Search Report from EP Appl. No. 12008499.1 mailed Apr. 10, 2013.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.

(56) References Cited

OTHER PUBLICATIONS

International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.™. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.™. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.™. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.™." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndot.Hill, vol. 111, (1984), pp. 2490-2499.
Cosman et al., "Radiofrequency Lesion Generation and its Effect on Tissue Impedance", Applied Neurophysiology, 51:230-242, 1988.
Comm et al., "Theoretical Aspects of Radiofrequency Lesions in the Dorsal Root Entry Zone" Neurosurgery 15:(1984), pp. 945-950.
Crawford et al., "Use of the LigaSure.™. Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).

(56) References Cited

OTHER PUBLICATIONS

Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.™. Vessel Sealing System: A Case Report" Innovations That Work, Feb. 2002.
Humphries Jr. et al., "Finite.cndot.Element Codes to Model Electrical Heating and Non.cndot.Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.™. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.™. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure.™. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.™. System Used in Laparoscopic 1st and 2nd Stage Orchiopexy" Innovations That Work, Nov. 2002.
K. Ogata, Modern Control Engineering, Prentice-Hall, Englewood Cliffs, N. J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.™. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
Mdtech product literature (Dec. 1999) "FlexStrand": product description, 1 page.
Mdtech product literature (Mar. 2000) I'D Wire: product description, 1 page.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
Chinese Office Action (With English Translation) and Search Report, dated Sep. 28, 2015, corresponding to Chinese Application No. 201310000926.6; 13 total pages.
Stagegaard, N., Petersen H.H., Chen X., Svendsen J.H., "Indication of the Radiofrequency Induced Lesion Size by are-ablation Measurements" Europace (2005) 7, 525-534.
U.S. Appl. No. 08/136,098, filed Oct. 14, 1993; Roger A. Stem.
U.S. Appl. No. 08/483,742, filed Jun. 7, 1995; Roger A. Stem.
European Examination Report from Application No. EP 03 736 458.5 dated Jul. 17, 2015.

SYSTEM AND METHOD FOR TREATING TISSUE USING AN EXPANDABLE ANTENNA

CROSS-REFERENCE TO RELATED APPLICATIONS

This application is a divisional application of U.S. application Ser. No. 13/344,790, now U.S. Pat. No. 9,119,648, filed on Jan. 6, 2012, the entire contents of which are incorporated by reference herein.

BACKGROUND

1. Technical Field

The present disclosure relates to electrosurgical ablation devices and methods. More particularly, the disclosure relates to treating tissue using a deployable antenna capable of being expanded.

2. Background of Related Art

In the treatment of diseases such as cancer, certain types of cancer cells have been found to denature at elevated temperatures that are slightly lower than temperatures normally injurious to healthy cells. These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great amount of control. This is partly why a more direct and precise method of applying microwave radiation has been sought.

Presently, there are several types of microwave probes in use, e.g., monopole, dipole, and helical. One type is a monopole antenna probe consisting of a single, elongated microwave conductor exposed at the end of the probe. The probe is sometimes surrounded by a dielectric sleeve. The second type of microwave probe commonly used is a dipole antenna consisting of a coaxial construction having an inner conductor and an outer conductor with a dielectric separating a portion of the inner conductor and a portion of the outer conductor. In the monopole and dipole antenna probe, microwave energy generally radiates perpendicularly from the axis of the conductor.

Because of the perpendicular pattern of microwave energy radiation, conventional antenna probes are typically designed to be inserted directly into the tissue, e.g., a tumor, to be radiated. However, such typical antenna probes commonly fail to provide uniform heating axially and/or radially about the effective length of the probe.

It is often difficult to assess the extent to which the microwave energy will radiate into the surrounding tissue, i.e., it is difficult to determine the area or volume of surrounding tissue that will be ablated. Furthermore, when conventional microwave antennas are inserted directly into the tissue, e.g., cancerous tissue, there is a potential of dragging or pulling cancerous cells along the antenna body into other parts of the body during insertion, placement, or removal of the antenna probe.

In certain circumstances, it is advantageous to create a relatively large ablation region, which often requires multiple ablation instruments inserted into a patient.

SUMMARY

As used herein the term "distal" refers to that portion of the microwave ablation device, or component thereof, farther from the user while the term "proximal" refers to that portion of the microwave ablation device or component thereof, closer to the user.

According to one aspect of the present disclosure, an ablation device is provided. The ablation device includes an antenna assembly having a radiating portion configured to deliver energy from a power source to tissue of a patient. The radiating portion has an outer conductor and an inner conductor extending therethrough. The inner conductor is disposed within the outer conductor and defines a longitudinal axis. One of the inner conductor and the outer conductor is movable relative to the other to cause at least a portion of the outer conductor to expand radially relative to the longitudinal axis.

Alternatively or in addition, the outer conductor may include a plurality of deployable conductors disposed at least partially along a length thereof configured to expand radially relative to the longitudinal axis.

Alternatively or in addition, the plurality of deployable conductors may be configured to mechanically cut through tissue.

Alternatively or in addition, the plurality of deployable conductors may be configured to cut through tissue with the aid of energy from the power source.

According to a further aspect of the present disclosure, at least a portion of the outer conductor may be flexible.

Alternatively or in addition, a distance between the outer conductors and the inner conductor may define an ablation region when the outer conductors are radially expanded relative to the longitudinal axis.

Alternatively or in addition, the outer conductor and the inner conductor may be configured to form an electromagnetic field within the ablation region upon actuation thereof.

Alternatively or in addition, distal movement of the outer conductor relative to the inner conductor may cause at least a portion of the outer conductor to expand radially relative to the longitudinal axis.

Alternatively or in addition, proximal movement of the inner conductor relative to the outer conductor may cause at least a portion of the outer conductor to expand radially relative to the longitudinal axis.

According to a further aspect of the present disclosure, a method of treating tissue is provided. The method includes the step of inserting at least a portion of a microwave ablation device into tissue. The microwave ablation device includes an inner conductor disposed within an outer conductor. The inner conductor defines a longitudinal axis. The method also includes the steps of expanding at least a portion of the outer conductor relative to the longitudinal axis to generate an ablation region between the outer conductor and the inner conductor and delivering energy to at least one of the inner conductor and the outer conductor to treat tissue disposed within the ablation region.

Alternatively or in addition, the expanding step of the method may further comprise the step of moving the inner conductor relative to the outer conductor.

Alternatively or in addition, the expanding step of the method may further comprise the step of moving the outer conductor relative to the inner conductor.

Alternatively or in addition, the method may also include the step of applying at least one of a distal force and a proximal force to the microwave ablation device subsequent to the expanding step to cut tissue.

Alternatively or in addition, the method may also include the step of providing energy to the outer conductor subsequent to the expanding step and prior to the applying step to cut tissue.

Alternatively or in addition, the method may also include the step of providing energy to the inner and outer conductors to generate a magnetic field within the ablation region configured to treat tissue.

Alternatively or in addition, the method may also include performing the expanding step to cut tissue.

According to a further aspect of the present disclosure, an electrosurgical system for treating tissue is provided. The system includes an electrosurgical generator and a microwave ablation device. The microwave ablation device includes a radiating portion configured to deliver energy from the electrosurgical generator to tissue of a patient. The radiating portion has an outer conductor and an inner conductor extending therethrough. The inner conductor is disposed within the outer conductor and defines a longitudinal axis. The microwave ablation device also includes a distal tip disposed in mechanical cooperation with at least one of the outer and inner conductors. One of the inner conductor and the outer conductor is movable along the longitudinal axis relative to the other such that the outer conductor expands radially relative to the longitudinal axis.

Alternatively or in addition, relative movement of the distal tip towards the distal end of the outer conductor may cause at least a portion of the outer conductor to expand radially relative to the longitudinal axis.

Alternatively or in addition, the outer conductor may be configured to separate into a plurality of conductors along at least a portion thereof. Alternatively or in addition, the conductors may be configured to expand relative to the longitudinal axis in response to relative proximal movement of the distal tip.

Alternatively or in addition, the inner conductor may be operably coupled to the distal tip such that movement of the inner conductor along the longitudinal axis translates relative movement of the distal tip.

BRIEF DESCRIPTION OF THE DRAWINGS

Various embodiments of the present disclosure are described herein with reference to the drawings wherein.

DETAILED DESCRIPTION

Figure 1:
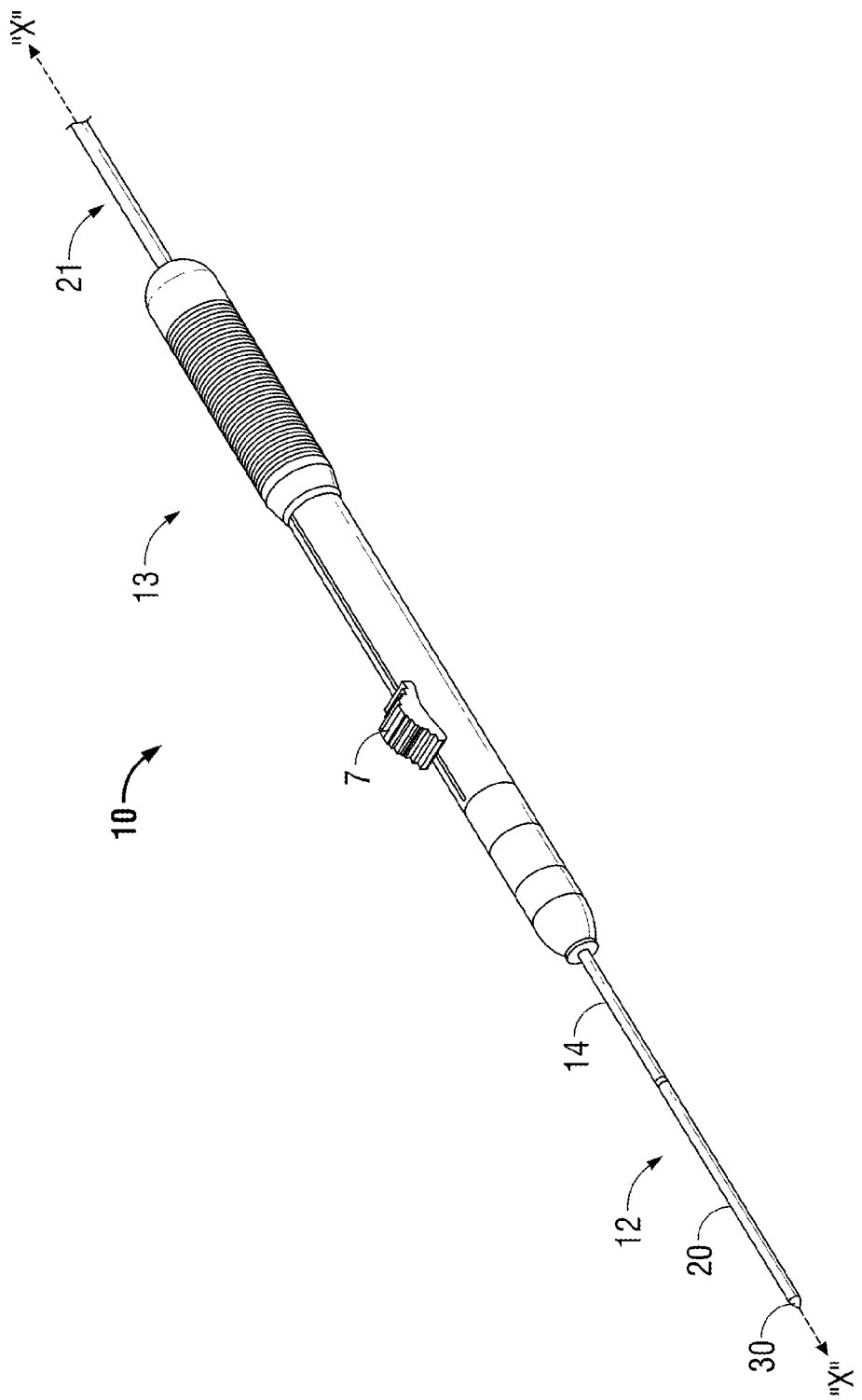
FIG. 1 shows a diagram of a microwave antenna assembly in accordance with an embodiment of the present disclosure.

Embodiments of the presently disclosed microwave ablation devices are described in detail with reference to the drawings, in which like reference numerals designate identical or corresponding elements in each of the several views.

An ablation device (e.g., a microwave ablation device) in accordance with the present disclosure is referred to in the figures as reference numeral 10. Referring initially to FIG. 1, microwave ablation device 10 includes a handle portion 13 and a microwave antenna 12 having a shaft or feedline 14. Feedline 14 includes an outer conductor 20 and an inner conductor 18, that defines a longitudinal axis X-X. A power transmission cord 21 is shown to connect microwave ablation device 10 to a suitable electrosurgical generator 22 (see FIG. 2). Additionally, an actuation element 7 is illustrated in FIG. 1 in accordance with various embodiments of the present disclosure.

Figure 2:
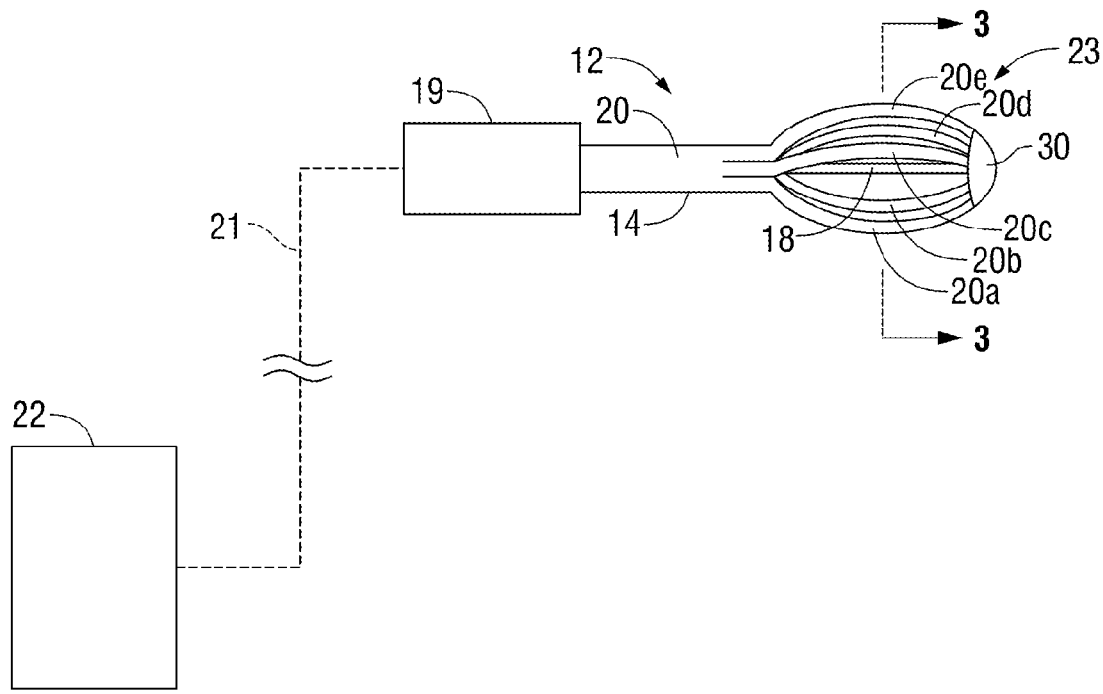
FIG. 2 is a schematic view of the microwave antenna assembly of FIG. 1 connected to a generator.

As seen in FIG. 2, a distal tip 30 is disposed adjacent to or coupled to a distal end of inner conductor 18 and/or outer conductor 20. In the illustrated embodiment, the proximal end of feedline 14 includes a coupler 19 that electrically couples antenna 12 to generator 22 via power transmission cord 21. As will be discussed in further detail below, outer conductor 20 includes a distal portion 23 configured to expand radially relative to longitudinal axis X-X such that distal portion 23 separates into a plurality of radially deployable conductors (e.g., conductors 20a, 20b, 20c, 20d, and 20e) upon actuation of actuation element 7.

Microwave ablation device 10 may be introduced to a treatment site via a straight, arcuate, non-deployable and/or deployable applicator or introducer. In embodiments, tip 30 is configured to pierce tissue to facilitate introduction of microwave ablation device 10 to the treatment site. Tip 30 may be insulative and/or formed of a dielectric material.

As described above and as shown in FIGS. 2 and 3, feedline 14 may be in the form of a coaxial cable. Portions of feedline 14 may be flexible and formed of outer conductor 20 surrounding inner conductor 18. Inner conductor 18 and/or outer conductor 20 may be made of a suitable conductive metal that may be semi-rigid or flexible, such as, for example, copper, gold, or other conductive metals with similar conductivity values. Alternatively, portions of inner conductor 18 and outer conductor 20 may also be made from stainless steel that may additionally be plated with other materials, e.g., other conductive materials, to improve their properties, e.g., to improve conductivity or decrease energy loss, etc.

Figure 3:
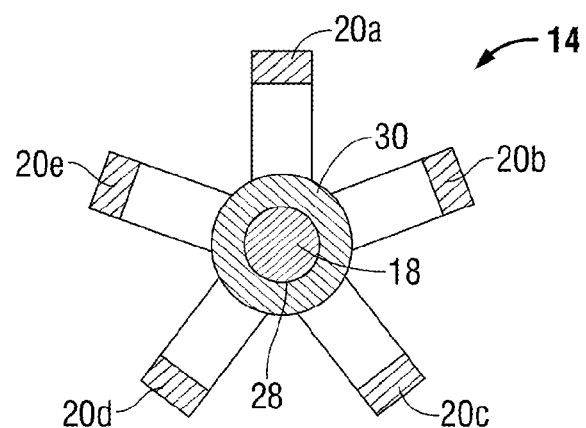
FIG. 3 is a cross-sectional view taken along section line 3-3 of FIG. 2.

With continued reference to FIG. 3, feedline 14 of antenna 12 is shown including a dielectric material 28 surrounding at least a portion of a length of inner conductor 18 and outer conductor 20 and/or conductors 20a-20e surrounding at least a portion of a length of dielectric material 28 and/or inner conductor 18. That is, a dielectric material 28 is interposed between inner conductor 18 and outer conductor 20, to provide insulation therebetween and may be comprised of any suitable dielectric material.

Figure 4:
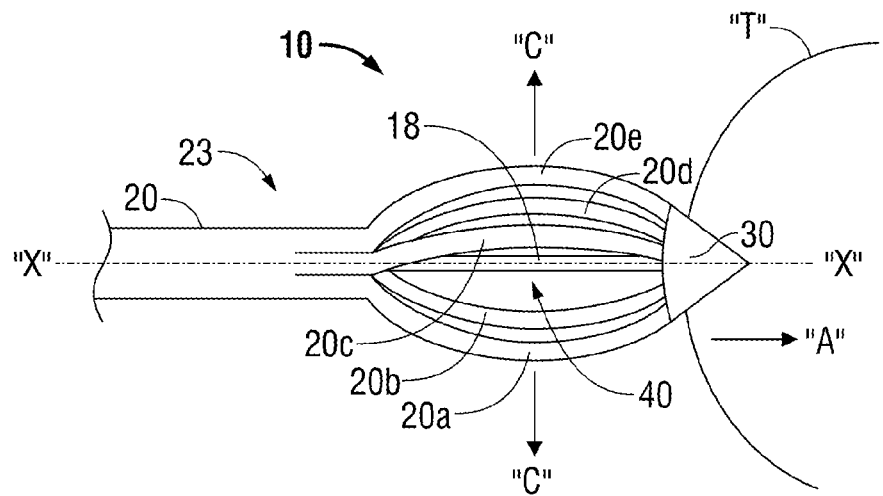
FIG. 4 is a side view of a distal portion of the microwave antenna assembly of FIGS. 1-3.
Figure 5:
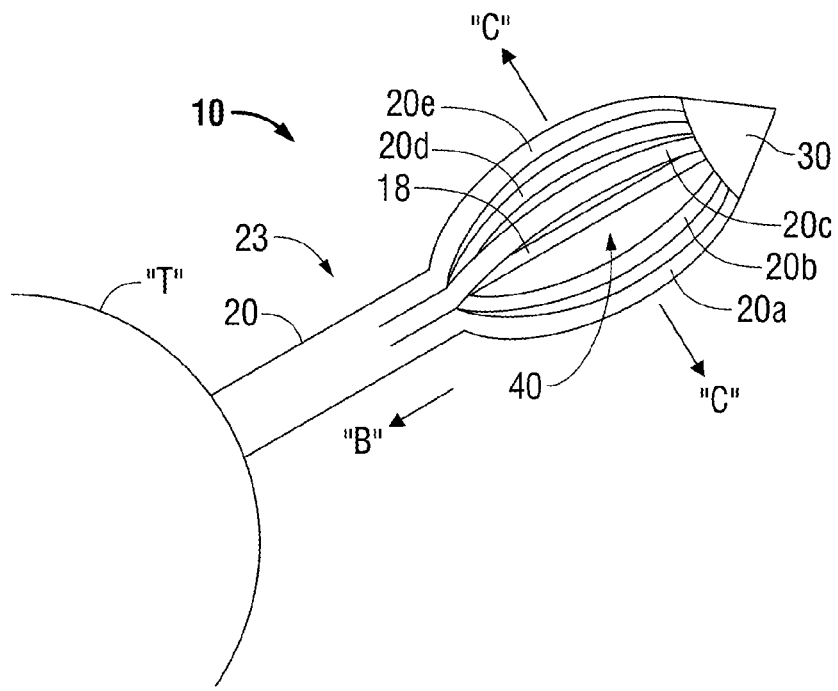
FIG. 5 is a perspective view of the distal portion of the microwave ablation device of FIGS. 1-4.

Referring now to FIGS. 4 and 5, the distal portion 23 of outer conductor 20 is separated into a plurality of radially deployable outer conductors 20a, 20b, 20c, 20d, and 20e. Conductors 20a-20e are illustrative only in that the distal portion 23 of outer conductor 20 may be separated into any two or more radially deployable conductors. Outer conductor 20 may be at least partially formed of a flexible material wherein separation of the distal portion 23 of outer conductor 20 into conductors 20a-20e may be achieved during the manufacturing process by cutting or slicing through the flexible material along at least a portion of the distal portion 23 of outer conductor 20 in multiple locations around the circumference of distal portion 23. Distal tip 30 is in mechanical cooperation with each conductor 20a-20e or inner conductor 18. In one embodiment, inner conductor 18 is movable relative to outer conductor 20 via translation of actuation element 7 (See FIG. 1), as discussed in detail below. In another embodiment, outer conductor 20 is movable relative to inner conductor 18 and distal tip 30, as discussed in detail below. In some embodiments, distal tip 30 is also in electrical communication with either outer conductors 20a-20e or inner conductor 18.

Translation of actuation element 7 (see FIG. 1) causes movement of inner conductor 18 (substantially along longitudinal axis X-X) with respect to outer conductor 20 or vice-versa. More specifically, distal translation of actuation element 7 causes inner conductor 18 to move distally in the direction of arrow "A" and proximal translation of actuation element 7 causes inner conductor 18 to move proximally in the direction of arrow "B." In response to proximal movement of inner conductor 18, the distal portion 23 of outer conductor 20 is forced or expanded radially relative to longitudinal axis X-X in the direction of arrow "C" (see FIGS. 4 and 5) such that outer conductor 20 separates into conductors 20a-20e. Thus, an ablation region 40, as defined by the boundaries of conductors 20a-20e (including the area between conductors 20a-20e and inner conductor 18), is expanded (e.g., widened) as a distance between conductors 20a-20e and inner conductor 18 becomes larger. In response to distal movement of inner conductor 18, conductors 20a-20e retract toward longitudinal axis X-X in the direction opposite to arrows "C".

In embodiments, at least a portion of each conductor 20a-20e is flexible to facilitate the radial expansion of conductors 20a-20e relative to longitudinal axis X-X. The ablation region 40 may be an electromagnetic field generated by opposing polarities of inner conductor 18 (e.g., positive) relative to conductors 20a-20e (e.g., negative) for ablating tissue disposed within the ablation region 40.

In one embodiment, translation of actuation element 7 (see FIG. 1) causes movement of outer conductor 20 (substantially along longitudinal axis X-X) with respect to inner conductor 18 and distal tip 30. In this embodiment, inner conductor 18 and distal tip 30 are stationary along the longitudinal axis X-X. More specifically, distal translation of actuation element 7 causes outer conductor 20 to move distally in the direction of arrow "A" and proximal translation of actuation element 7 causes outer conductor 20 to move proximally in the direction of arrow "B." In response to distal movement of outer conductor 20, the distal portion 23 of outer conductor 20 is forced or expanded radially relative to longitudinal axis X-X, in the direction of arrow "C" (see FIGS. 4 and 5) such that outer conductor 20 separates into conductors 20a-20e. In response to proximal movement of outer conductor 20, conductors 20a-20e retract toward longitudinal axis X-X in the direction opposite to arrow "C".

Each conductor 20a-20e may be configured to pierce or slice through tissue, either mechanically and/or with the aid of energy, e.g., radiofrequency energy, heat energy, resistive energy, etc. In the embodiment where conductors 20a-20e can mechanically pierce or slice through tissue, conductors 20a-20e may be thin enough to pierce or slice through tissue upon the exertion of a predetermined amount of force (e.g., the amount of force generated upon retraction of inner conductor 18 and/or radial expansion of conductors 20a-20e). In other words, antenna 12 is positioned within tissue when conductors 20a-20e are disposed in a non-expanded, parallel configuration relative to the longitudinal axis X-X and then the conductors 20a-20e are expanded to pierce into and through tissue. As a result thereof, tissue is embedded within the ablation zone 40 for treatment. Additionally or alternatively, conductors 20a-20e may be configured to conduct energy, e.g., from generator 22, to slice or pierce through tissue. Deployment of conductors 20a-20e also helps secure the antenna 12 relative to a tumor and maintain the antenna 12 in place during treatment.

Referring specifically to FIG. 4, conductors 20a-20e are shown radially expanded relative to the longitudinal axis X-X prior to insertion of antenna 12 into tissue "T". In this scenario, a distal force applied to antenna 12 in the direction of arrow "A" causes conductors 20a-20e to slice through the tissue "T" such that at least a portion of tissue "T" is disposed within ablation region 40.

Referring specifically to FIG. 5, antenna 12 is shown inserted into or through tissue "T" prior to radial expansion of conductors 20a-20e relative to the longitudinal axis X-X. In this scenario, a proximal force applied to antenna 12 in the direction of arrow "B" causes conductors 20a-20e to slice through tissue "T" such that at least a portion of tissue "T" is disposed within ablation region 40.

As discussed above, conductors 20a-20e may be configured to pierce or slice through tissue mechanically and/or with the aid of energy from generator 22. In the case of conductors 20a-20e utilizing the aid of energy from generator 22 to pierce or slice through tissue, conductors 20a-20e may be energized prior to engagement with tissue "T" or, alternatively, substantially simultaneously therewith.

By retracting and expanding the conductors 20a-20e during a procedure, the effective length and impedance of the antenna 12 is changed, thereby changing the performance of the antenna 12. In this manner, the antenna 12 may be actively tuned during a procedure.

Figure 6A:
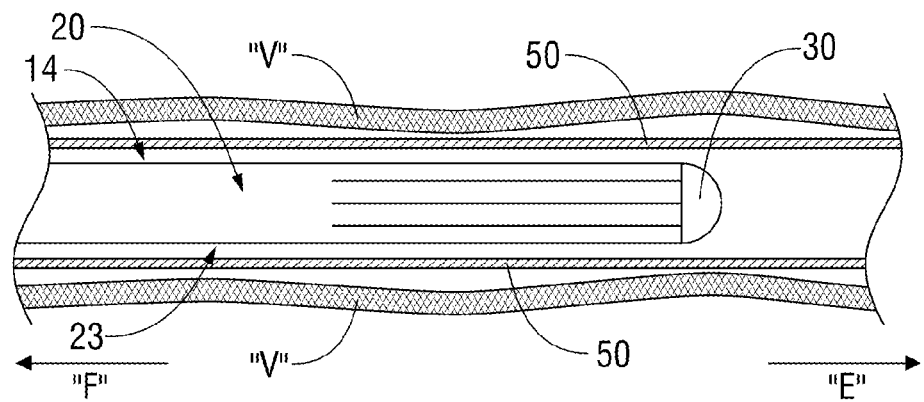
FIG. 6A is a side view of the distal portion of the microwave ablation device of FIGS. 1-5 unexpanded and disposed within a vessel.
Figure 6B:
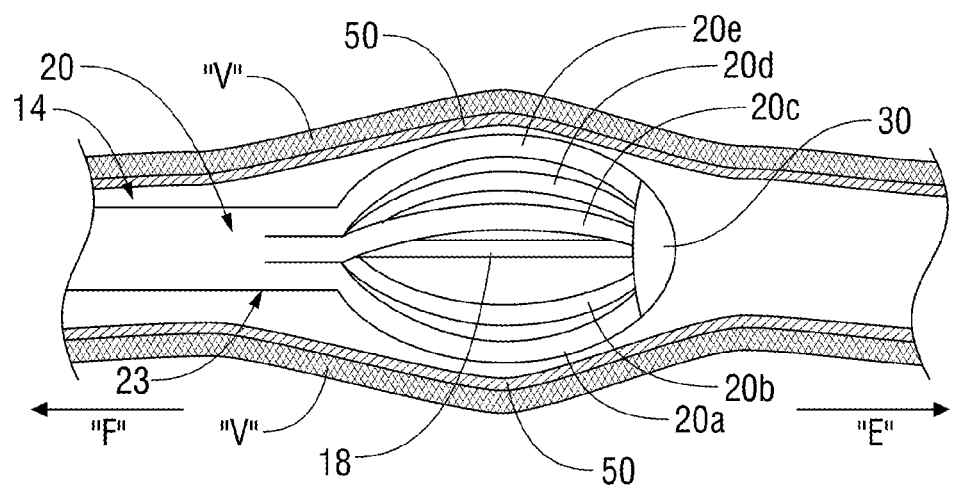
FIG. 6B is a side view of the distal portion of the microwave ablation device of FIGS. 1-6 expanded and disposed within the vessel.

Referring now to FIGS. 6A and 6B, feedline 14 is shown disposed within a vessel "V". A vessel repairing sealant 50 (e.g., fibrin or elastic/collagen matrix) is disposed between an inner wall of vessel "V" and outer conductor 20 and is configured to repair the inner walls of vessel "V" once properly deployed. Sealant 50 may be, for example, a sleeve and/or a mesh matrix configured to be slid over at least a portion of feedline 14 such that upon deployment of feedline 14 within vessel "V", sealant 50 is disposed between the inner surface of vessel "V" and at least a portion of feedline 14. As illustrated in FIG. 6A, feedline 14 is inserted within vessel "V" while conductors 20a-20e are disposed in a non-expanded or retracted state relative to longitudinal axis X-X. Once feedline 14 is positioned relative to sealant 50 within vessel "V", actuation element 7 is translated proximally in the direction of arrow "F" to retract inner conductor 18, thereby pulling distal tip 30 proximally to force conductors 20a-20e to expand radially relative to longitudinal axis X-X. As discussed above, actuation element 7 may, in certain embodiments, be translated distally in the direction of arrow "E" to move outer conductor 20 distally to engage distal tip 30, thereby forcing conductors 20a-20e to expand radially relative to the longitudinal axis X-X.

In either scenario, radial expansion of conductors 20a-20e forces sealant 50 to engage the inner wall of vessel "V" to repair cracks or damaged areas in the vessel "V", as shown in FIG. 6B. In embodiments, once sealant 50 engages the inner wall of vessel "V", generator 22 is configured to selectively supply energy (e.g., RF or microwave energy) to conductors 20a-20e to activate or cure sealant 50 via the generation of heat. That is, sealant 50 may be a mesh matrix having vessel repairing gel or collagen disposed thereon that is configured to leach to the inner wall of vessel "V" upon the application of heat caused by the supply of energy through conductors 20a-20e and/or inner conductor 18. Examples of such vessel repairing sealants include, without limitation, Evicel® liquid fibrin sealant and the CryoSeal® FS system.

Once a desired portion of sealant 50 is applied to the inner wall of vessel "V", conductors 20a-20e may be radially retracted toward longitudinal axis X-X via actuation of actuation element 7 such that antenna 12 is movable proximally (arrow "F") or distally (arrow "E") within vessel "V" for purposes of removal therefrom or for purposes of movement relative to sealant 50, as shown in FIG. 6A. In this manner, distal portion 23 of outer conductor 20 may be positioned or re-positioned to substantially align with a portion of sealant 50 that has not yet been forced to engage the inner wall of vessel "V" and/or been activated or cured by the application of heat generated by the supply of energy through conductors 20a-20e and/or inner conductor 18.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A method of treating tissue, comprising:
   inserting at least a portion of a microwave ablation device into tissue, the microwave ablation device defining a longitudinal axis and including an inner conductor disposed within an outer conductor, the inner and outer conductors separated by a dielectric material, the dielectric material disposed on the inner conductor;
   expanding at least a portion of the outer conductor relative to the longitudinal axis to generate an ablation region between the outer conductor and the inner conductor; and
   delivering energy to at least one of the inner conductor or the outer conductor to treat tissue disposed within the ablation region.

2. A method according to claim 1, wherein expanding at least a portion of the outer conductor relative to the longitudinal axis includes moving the inner conductor relative to the outer conductor.

3. A method according to claim 1, wherein expanding at least a portion of the outer conductor relative to the longitudinal axis includes moving the outer conductor relative to the inner conductor.

4. A method according to claim 1, further comprising applying at least one of a distal force or a proximal force to the microwave ablation device to cut tissue subsequent to expanding at least a portion of the outer conductor relative to the longitudinal axis.

5. A method according to claim 4, further comprising providing energy to the outer conductor to cut tissue subsequent to expanding at least a portion of the outer conductor relative to the longitudinal axis and prior to applying at least one of a distal force or a proximal force to the microwave ablation device.

6. A method according to claim 5, further comprising providing energy to the inner and outer conductors to generate a magnetic field within the ablation region.

7. A method according to claim 4, further comprising cutting tissue by expanding at least a portion of the outer conductor relative to the longitudinal axis.

8. A method according to claim 1, wherein expanding at least a portion of the outer conductor relative to the longitudinal axis includes moving the inner conductor relative to the dielectric material.

9. A method according to claim 1, wherein expanding at least a portion of the outer conductor relative to the longitudinal axis includes moving the outer conductor relative to the dielectric material.

10. A method according to claim 1, further comprising radially expanding a plurality of outer conductors disposed at least partially along a length of the outer conductor.

11. A method according to claim 1, further comprising cutting through tissue by radially expanding a plurality of outer conductors disposed at least partially along a length of the outer conductor and delivering energy to the plurality of outer conductors.

12. A method according to claim 1, wherein expanding at least a portion of the outer conductor relative to the longitudinal axis includes distally moving the outer conductor relative to the inner conductor.

13. A method according to claim 1, wherein expanding at least a portion of the outer conductor relative to the longitudinal axis includes proximally moving the inner conductor relative to the outer conductor.

* * * * *